(12) United States Patent
Hsieh et al.

(10) Patent No.: US 6,476,186 B1
(45) Date of Patent: Nov. 5, 2002

(54) PROCESS FOR PREPARING OCTREOTIDE AND DERIVATIVES THEREOF

(75) Inventors: Yao-Tsung Hsieh, Kaohsiung; Shiang-Rong Chang; Shyh-Yi Chyi, both of Tau Yen; Hui-Lan Wu, Kaohsiung; Shu-Ling Chen, Chiai Hsien; Henton Huang, Tau Yen; Te-Wei Lee, Taipei; Tian-Fu Huang, Tau Yen, all of (TW)

(73) Assignee: Institute of Nuclear Energy Research, Tau Yen (TW)

( * ) Notice: Subject to any disclaimer, the term of this patent is extended or adjusted under 35 U.S.C. 154(b) by 0 days.

(21) Appl. No.: 09/576,769

(22) Filed: May 24, 2000

(51) Int. Cl.$^7$ ............. C07K 1/04; C07K 1/08; C07K 14/655

(52) U.S. Cl. ........................ 530/311; 530/334

(58) Field of Search .................. 530/311, 328, 530/334, 345; 514/9, 11, 16

(56) References Cited

U.S. PATENT DOCUMENTS 5,889,146 A * 3/1999 Lee et al. .................. 530/317

FOREIGN PATENT DOCUMENTS

EP 824103 * 2/1998

OTHER PUBLICATIONS

Arano et al. Conventional and High–Yield Synthesis of OTPA . . . Bioconjugate Chem. vol. 8, No. 3, pp. 442–446, 1997.*

Volkmer–Engert et al. Charcoal Surface–Assisted Catalysis . . . J. Peptide Res. vol. 51, pp. 365–369, 1998.*

* cited by examiner

*Primary Examiner*—Jeffrey E. Russel
(74) *Attorney, Agent, or Firm*—Rosenberg, Klein & Lee

(57) ABSTRACT

This invention relates a process for preparing octreotide and derivatives thereof. The starting material, Thr(ol)(tBu)-2-chlorotrityl resin is coupled with the various amino acids. The straight peptide-resin of D-Phe-Cys(Trt)-Phe-D-Trp(Boc)-Lys(Boc)-Thr(tBu)-Cys(Trt)-Thr(ol)(tBu)-2-chlorotrityl resin or D-Phe-Cys(Trt)-Tyr(tBu)-D-Trp(Boc)-Lys(Boc)-Thr(tBu)-Cys(Trt)-Thr(ol)(tBu)-2-chlorotrityl resin was obtained. Cleavage of the peptide from the resin was achieved by strong acid solution. The cleaved peptide reacted with charcoal to give disulfide-containing peptide of

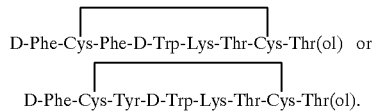

6 Claims, No Drawings

PROCESS FOR PREPARING OCTREOTIDE AND DERIVATIVES THEREOF

FIELD OF THE INVENTION

The present invention relates to a novel synthesis of octreotide and derivatives thereof by solid phase peptide synthesis. In particular, the present invention relates to synthesize linear peptides, cleave from resin and the cyclization process for their preparation.

BACKGROUND OF THE INVENTION

Octreotide is a somatostatin analog which is inhibited the growth of tumor cell by binding the analog to the somatostatin receptor that located on the surface of tumor cell. The high binding affinity of the octreotide with the somatostatin receptor has been utilized as a tumor-visualization agent by labeled the octreotide with radioisotope. In-DTPA-octreotide (Octreo-Scan III) have been successfully used to visualized somatostatin receptor-positive tumors by gamma camera scintigraphy.

Octreotide comprises 8 amino acids which has the following structural formula:

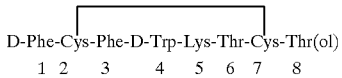
  1 2   3   4  5  6  7   8 wherein sulfur atoms of the Cys at the position 2 and of the Cys at the position 7 are mono-cyclic to form an -S-S- bridge. Tyr-3-octreotide is a octreotide derivative thereof which Phe at the position 3 is replaced by Tyr.

Synthesis of octreotide and derivative thereof can be carried out by two methods. The first method is synthesized initially by fragment condensation solution phase procedures. The synthetic process of octreotide has been described by Bauer et al (Eur. Pat. Appl. 29,579,1981 and U.S. Pat. No. 4,395,403, 1983).

The process comprises: <i> removing protected group from peptide; <ii> linking together by an amide bond two peptide unit; <iii> converting a function group at the N- or C-terminal; <iv> oxidizing a straight chain polypeptide by boron tristrifluoroacetate. This process involves a time-consuming, multi-step synthesis, and it is difficult to separate octreotide from the reaction mixtures since all the synthesis steps are carried out in liquid phase.

The second method is synthesized by solid-phase procedures. Edward et al isolated side chain protected [D-Trp(Boc)[4], Lys(Boc)[5], Thr(Bu$^t$)[6]]-octreotide with a total yield of 14% by cleaving the protected peptide from the resin with threoninol (J. Med. Chem. 1994,37,3749–3757). Arano et al carried out another solid phase method for DTPA-octreotide (Bioconjugate Chem. 1997,8,442–446). Iodine oxidation of the DTPA-peptide produced DTPA-D-Phe$^1$-octreotide in overall 31.8% yield based on the starting Fmoc-Thr(tBu)-ol-resin.

Wu et al developed a method to synthesis of octreotide (Tetrahedron Letters 1998,39,1783–1784). The formation of the disulfide bond was oxidized using a dilution solution of octreotide with air and spent 48 hours. Lee et al recently have carried out a new method to anchor Thr(ol) to a solid phase synthesis resin for preparation of octreotide (U.S. Pat. No. 5,889,146, 1999). Fmoc-Thr(ol)-terephthal-acetal was loaded onto the resin. After construction of peptide chains by Fmoc chemistry, cyclization of the peptide may be obtained on resin by oxidation with iodine. The cleavage of peptide-resin with trifluoroacetic acid, produced octreotide with overall yield of >70% from the starting Fmoc-Thr(ol)-terephthal-acetal-resin. All of these procedures completed the cyclization of the octreotide either on totally deprotected peptide or on the resin.

SUMMARY OF THE INVENTION

The main object of the present invention is to provide a novel process for synthesis of octreotide and derivatives thereof. The starting material, Thr(ol)(tBu)-2-chlorotrityl resin is coupled with the various amino acids. The straight peptide-resin, such as
D-Phe-Cys(Trt)-Phe-D-Trp(Boc)-Lys(Boc)-Thr(tBu)-Cys(Trt)-Thr(ol)(tBu)-2-chlorotrityl resin or
D-Phe-Cys(Trt)-Tyr(tBu)-D-Trp(Boc)-Lys(Boc)-Thr(tBu)-Cys(Trt)-Thr(ol)(tBu)-2-chlorotrityl resin was obtained. Cleavage of the peptide from the resin was achieved by strong acid solution.

The cleaved peptide reacted with charcoal to give disulfide-containing peptide as following:

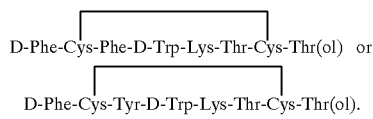

Purification of the crude peptide was obtained by chromatography. The novel process in this invention for synthesis of octreotide and derivative thereof has been proved to be more time-saving, higher yield >80%, and easier for separation from the reaction system than the prior art is.

DETAILED DESCRIPTION OF THE INVENTION

The following abbreviations are employed:
Fmoc: 9-fluorenylmethoxycarbonyl
Boc: t-butyloxycarbonyl
tBu: tert-butyl
Trt: triphenylmethyl
Thr(ol): the threoninol residue
Phe: the phenylalanine residue
Cys: the cysteine residue
Thr: the threonine residue
Lys: the lysine residue
Trp: the tryptophan residue
Tyr: the tyrosine residue
TFA: trifluoroacetic acid
EDT: 1,2-ethanedithiol
THF: tetrahydrofuran
HBTB: Benzotriazolyloxytetramethyluronium hexafluorophosphate

EXAMPLE 1-1

Synthesis of D-Phe-Cys(Trt)-Phe-D-Trp(Boc)-Lys(Boc)-Thr(tBu)-Cys(Trt)-Thr(ol)(tBu)-2-chlorotrityl resin.

Thr(ol)(tBu)-2-chlorotrityl resin (1.0 mmol, 1.25 g) was used as the starting material for solid phase peptide synthesis. Fmoc-Cys(Trt)-OH (3 mmol, 1.75 g) was activated by using HBTU. In the coupling step, the activated Fmoc-Cys(Trt)-OH reacted with Thr(ol)(tBu)-2-chlorotrityl resin to form Fmoc-Cys(Trt)-Thr(ol)(tBu)-2-chlorotrityl resin. The Fmoc protecting group of Fmoc-Cys(Trt)-Thr(ol)(tBu)-2-chlorotrityl resin was removed by piperidine. Activating, coupling and deprotecting steps are repeated with each subsequent amino acid until an assembly chain D-Phe-Cys(Trt)-Phe-D-Trp(Boc)-Lys(Boc)-Thr(tBu)-Cys(Trt)-Thr(ol)

(tBu)-2-chlorotrityl resin has been completed. The peptide resin was dried in vacuo and weighted to be 2.89 g.

EXAMPLE 1-2

Synthesis of D-Phe-Cys-Phe-D-Trp-Lys-Thr-Cys-Thr(ol)

The D-Phe-Cys(Trt)-Phe-D-Trp(Lboc)-Lys(Boc)-Thr(tBu)-cys(Trt)-Thr(ol)(tBu)-2-chlorotrityl resin (2.89 g) was cleaved with 9.5%TFA-2.5%EDT-2.5%$H_2O$ solution at room temperature for 1.5 hours. The cleavage mixtures were dried to about 0.5~1.0 ml under vacuum. After adding with equal volume of ice-cold ether, these extracts were centrifuged. The pellets were collected and washed with cold dry ether. The cleavage products were extracted with 50% acetonitrile and dried by lyophilization to white powder. The crude peptide (0.9 g) was obtained and analyzed on a Waters HPLC, consisting of two 600E solvent pumps and a Waters 991 photodiode detector. Injections of 50 μl were eluted at a flow rate of 1.6 ml/min from a 10×250 mm C-18 reverse phase column, minitored at 280 nm. A 30 min linear gradient, from 80%~20% A (solvent A: 0.1% TFA in $H_2O$; solvent B: 0.1% TFA in acetonitrile) was used. The major peak at a retention time of 22.3 min was collected. ESMS analysis of the isolated peak showed $[M+H]^+=1021.8$ Da.

EXAMPLE 1-3

Synthesis of D-Phe-Cys-Phe-D-Trp-Lys-Thr-Cys-Thr(ol) (octreotide)

The D-Phe-Cys-Phe-D-Trp-Lys-Thr-Cys-Thr(ol)(0.9 g) dissolved in $H_2O$ to final concentration of 100 mg/ml. The solution was adjusted with 10% sodium hydroxide to pH 8.0. After adding with equal volume of acetonitrile, granulated charcoal (trace amount) was added to peptide solution. The resulting mixture was then stirred at room temperature for 5 hours and separated by filtration with 0.45 um PVDF membrane. The filtrate was dried by lyophilization to white powder. The crude peptide (0.85 g) was purified by chromatography using carboxy-methoxy-sepharose gel.

Analytical RP-HPLC of the octreotide was performed on a 10×250 mm C-18 column using a gradient of 80%~20% A in 30 min at a flow rate of 1.6 ml/min where A=0.1% TFA in $H_2O$ and B=0.1% TFA in acetonitrile. The product peak eluting at 20.7 min gave $[M+H]^+=1019.8$ Da by ESMS.

EXAMPLE 2-1

Synthesis of D-Phe-Cys(Trt)-Tyr(tBu)-D-Trp(Boc)-Lys(Boc)-Thr(tBu)-Cys(Trt)-Thr(ol)(tBu)-2-chlorotrityl resin.

Thr(ol)(tBu)-2-chlorotrityl resin (1.0 mmol. 1.25 g) was used as the starting material for solid phase peptide synthesis. Fmoc-Cys(Trt)-OH (3.0 mmol, 1.75 g) was activated by using HBTU. In the couplings step. the activated Fmoc-Cys(Trt)-OH reacted with Thr(ol)(tBu)-2-chlorotrityl resin to form Fmoc-Cys(Trt)-Thr(ol)(tBu)-2-chlorotrityl resin. The Fmoc protecting group of Fmoc-Cys(Trt)-Thr(ol)(tBu)-2-chlorotrityl resin was removed by piperidine. Activating, coupling and deprotecting steps are repeated with each subsequent amino acid until an assembly chain D-Phe-Cys(Trt)-Tyr(tBu)-D-Trp(Boc)-Lys(Boc)-Thr(tBu)-Cys(Trt)-Thr(ol)(tBu)-2-chlorotrityl resin has been completed. The peptide resin was dried in vacuo and weighted to be 2.91 g.

EXAMPLE 2-2

Synthesis of D-Phe-Cys-Tyr-D-Trp-Lys-Thr-Cys-Thr(ol)

The D-Phe-Cys(Trt)-Tyr(tBu)-D-Trp(Boc)-Lys(Boc)-Thr(tBu)-Cys(Trt)-Thr(ol)(tBu)-chlorotrityl resin (2.91 g) was cleaved with 95%TFA-2.5%EDT-2.5%$H_2O$ solution at room temperature for 1.5 hours. The cleavage mixtures were dried to about 0.5~1.0 ml under vacuum. After adding with equal volume of ice-cold ether, these extracts were centrifuged. The pellets were collected and washed with cold dry ether. The cleavage products were extracted with 50% acetonitrile and dried by lyophilization to white powder. The crude peptide (0.9 g) was obtained and analyzed on a Waters HPLC, consisting of two 600E solvent pumps and a Waters 991 photodiode detector. Injections of 50 μl were eluted at a flow rate of 1.6 ml/min from a 10×250 mm C-18 reverse phase column, minitored at 280 nm. A 40 min linear gradient, from 80%~20% A (solvent A: 0.1%TFA in $H_2O$; solvent B: 0.1%TFA in acetonitrile) was used. The major peak at a retention time of 20.2 min was collected. ESMS analysis of the isolated peak showed $[M+H]^+=1037.4$ Da.

EXAMPLE 2-3

Synthesis of D-Phe-Cys-Tyr-D-Trp-Lys-Thr-Cys-Thr(ol) (Tyr-3-octreotid e

The D-Phe-Cys-Tyr-D-Trp-Lys-Thr-Cys-Thr(ol) (0.9.g) dissolved in $H_2O$ to final concentration of 100 mg/ml. The solution was adjusted with 10% sodium hydroxide to pH8.0. After adding with equal volume of acetonitrile. granulated charcoal (trace amount) was added to peptide solution. The resulting mixture was then stirred at room temperature for 5 hr and separated by filtration with 0.45 μm PVDF membrane. The filtrate was dried by lyophilization to white powder. The crude peptide (0.85 g) was purified by chromatography using carboxy-methoxy-sepharose gel. Analytical RP-HPLC of the Tyr-3-octreotide was performed on a 10×250 mm C-18 column using a gradient of 80%~20% A in 30 min at a flow rate 1.6 ml/min where A=0.1%TFA in $H_2O$ and B=0.1%TFA in acetonitrile. The product peak eluting at 18.5 min gave $[M+H]^+=1019.8$ Da by ESMS.

What is claimed is:

1. A method for preparing octreotide (IA) comprising the following steps:

(IA)

D-Phe-Cys-Phe-D-Trp-Lys-Thr-Cys-Thr(ol).

(1) activating Fmoc-xxx(yyy)-OH through the addition of Benzotriazolyloxytetramethyluronium hexafluorophosphate, where initially xxx is Cys and yyy is Trt;

(2) coupling said activated Fmoc-xxx(yyy)-OH with a straight chain resin, said straight chain resin initially being Thr(ol)(tBu)-2-chlorotrityl resin, to form a Fmoc-protected straight chain resin;

(3) removing said Fmoc through the addition of piperidine to form said straight chain resin;

(4) repetitively repeating steps (1), (2) and (3) in consecutive order for producing a straight chain peptide-resin compound where xxx and yyy are substituted in the following order: xxx is Thr and yyy is tBu; xxx is Lys and yyy is Boc; xxx is D-Trp and yyy is Boc; xxx is Phe and yyy is absent; xxx is Cys and yyy is Trt; and xxx is D-Phe and yyy is absent;

(5) cleaving said straight chain peptide-resin compound of step (4) with strong acid to obtain a straight chain peptide compound; and (6) reacting said straight chain peptide compound of step (5) with charcoal to obtain the octreotide (IA).

2. The method according to claim 1, wherein the straight chain peptide-resin compound is formula (IIA), wherein (IIA) is D-Phe-Cys(Trt)-Phe-D-Trp(Boc)-Lys(Boc)-Thr(tBu)-Cys(Trt)-Thr(ol)(tBu)-2-chlorotrityl resin.

3. The method according to claim 1, wherein in step (5), the strong acid comprises TFA, EDT and H$_2$O solution.

4. A method for preparing derived octreotide (IB) comprising the following steps:

(IB)

D-Phe-Cys-Tyr-D-Trp-Lys-Thr-Cys-Thr(ol).

(1) activating Fmoc-xxx(yyy)-OH through the addition of Benzotriazolyloxytetramethyluronium hexafluorophosphate, where initially xxx is Cys and yyy is Trt;

(2) coupling said activated Fmoc-xxx(yyy)-OH with a straight chain resin, said straight chain resin initially being Thr(ol)(tBu)-2-chlorotrityl resin, to form a Fmoc-protected straight chain resin;

(3) removing said Fmoc through the addition of piperidine to form said straight chain resin;

(4) repetitively repeating steps (1), (2) and (3) in consecutive order for producing a straight chain peptide-resin compound where xxx and yyy are substituted in the following order: xxx is Thr and yyy is tBu; xxx is Lys and yyy is Boc; xxx is D-Trp and yyy is Boc; xxx is Tyr and yyy is tBu; xxx is Cys and yyy is Trt; and xxx is D-Phe and yyy is absent;

(5) cleaving said straight chain peptide-resin compound of step (4) with strong acid to obtain a straight chain peptide compound; and (6) reacting said straight chain peptide compound of step (5) with charcoal to obtain the octreotide (IB).

5. The method according to claim 4, wherein the straight chain peptide-resin compound is formula (IIB), wherein (IIB) is D-Phe-Cys(Trt)-Tyr(tBu)-D-Trp(Boc)-Lys(Boc)-Thr(tBu)-Cys(Trt)-Thr(ol)(tBu)-2-chlorotrityl resin.

6. The method according to claim 4, wherein in step (5), the strong acid comprises TFA, EDT and H$_2$O solution.

* * * * *